United States Patent
Peterson et al.

(10) Patent No.: US 11,627,887 B2
(45) Date of Patent: Apr. 18, 2023

(54) PPG SENSOR HAVING LIGHT ARRIVAL ANGLE CONTROL AT DETECTOR

(71) Applicant: Apple Inc., Cupertino, CA (US)

(72) Inventors: Rui L. Peterson, San Jose, CA (US); Chin San Han, Mountain View, CA (US)

(73) Assignee: Apple Inc., Cupertino, CA (US)

( * ) Notice: Subject to any disclaimer, the term of this patent is extended or adjusted under 35 U.S.C. 154(b) by 212 days.

(21) Appl. No.: 16/904,356

(22) Filed: Jun. 17, 2020

(65) Prior Publication Data

US 2020/0315473 A1 Oct. 8, 2020

Related U.S. Application Data

(63) Continuation of application No. 15/274,918, filed on Sep. 23, 2016, now Pat. No. 10,687,717.

(60) Provisional application No. 62/235,188, filed on Sep. 30, 2015.

(51) Int. Cl.
*A61B 5/024* (2006.01)
*A61B 5/1455* (2006.01)
*A61B 5/00* (2006.01)

(52) U.S. Cl.
CPC ...... *A61B 5/02416* (2013.01); *A61B 5/02438* (2013.01); *A61B 5/14551* (2013.01); *A61B 5/681* (2013.01); *A61B 5/7275* (2013.01); *A61B 2562/0238* (2013.01); *A61B 2562/0242* (2013.01); *A61B 2562/046* (2013.01)

(58) Field of Classification Search
CPC ............ A61B 5/02416; A61B 5/02438; A61B 5/14551; A61B 5/681; A61B 5/7275; A61B 5/02427; A61B 5/14552; A61B 5/0261; A61B 5/0059; A61B 2562/0238; A61B 2562/3242; A61B 2562/046

See application file for complete search history.

(56) References Cited

U.S. PATENT DOCUMENTS

| | | | |
|---|---|---|---|
| 5,483,261 | A | 1/1996 | Yasutake |
| 5,488,204 | A | 1/1996 | Mead et al. |
| 5,825,352 | A | 10/1998 | Bisset et al. |

(Continued)

FOREIGN PATENT DOCUMENTS

| | | |
|---|---|---|
| GB | 2524160 | 9/2015 |
| JP | 2000-163031 | 6/2000 |

(Continued)

OTHER PUBLICATIONS

Lee, S.K. et al. (Apr. 1985). "A Multi-Touch Three Dimensional Touch-Sensitive Tablet," Proceedings of CHI: ACM Conference on Human Factors in Computing Systems, pp. 21-25.

(Continued)

*Primary Examiner* — Tammie K Marlen
(74) *Attorney, Agent, or Firm* — Brownstein Hyatt Farber Schreck, LLP

(57) ABSTRACT

The present disclosure generally relates to wearable devices and methods for measuring a photoplethysmographic (PPG) signal. The wearable devices and methods described herein are capable of obtaining PPG signals by employing a PPG sensor array configured to receive light at angles associated with a high perfusion index. Viewing components may be coupled to the PPG sensor array to effect transmission of light at these preferential angles.

17 Claims, 9 Drawing Sheets

(56) References Cited

U.S. PATENT DOCUMENTS

| | | | |
|---|---|---|---|
| 5,835,079 | A | 11/1998 | Shieh |
| 5,880,411 | A | 3/1999 | Gillespie et al. |
| 6,188,391 | B1 | 2/2001 | Seely et al. |
| 6,310,610 | B1 | 10/2001 | Beaton et al. |
| 6,323,846 | B1 | 11/2001 | Westerman et al. |
| 6,690,387 | B2 | 2/2004 | Zimmerman et al. |
| 7,015,894 | B2 | 3/2006 | Morohoshi |
| 7,184,064 | B2 | 2/2007 | Zimmerman et al. |
| 7,616,110 | B2 | 11/2009 | Crump et al. |
| 7,663,607 | B2 | 2/2010 | Hotelling et al. |
| 7,676,253 | B2 | 3/2010 | Rarldan, Jr. |
| 8,378,811 | B2 | 2/2013 | Crump et al. |
| 8,479,122 | B2 | 7/2013 | Hotelling et al. |
| 8,618,930 | B2 | 12/2013 | Papadopoulos et al. |
| 9,526,642 | B2 | 12/2016 | Papadopoulos et al. |
| 9,826,905 | B2 | 11/2017 | Addison et al. |
| 10,681,717 | B2 | 6/2020 | Peterson et al. |
| 2006/0197753 | A1 | 9/2006 | Hotelling |
| 2012/0078116 | A1 | 3/2012 | Yamashita |
| 2014/0187992 | A1 | 7/2014 | Wilmering |
| 2014/0364707 | A1* | 12/2014 | Kintz .................. A61B 5/1459 600/310 |
| 2016/0022220 | A1* | 1/2016 | Lee .................... A61B 5/02433 600/479 |
| 2016/0242659 | A1 | 8/2016 | Yamashita et al. |
| 2017/0202466 | A1 | 7/2017 | Paulussen et al. |

FOREIGN PATENT DOCUMENTS

| | | |
|---|---|---|
| JP | 2002-342033 | 11/2002 |
| KR | 0100091592 | 8/2010 |

OTHER PUBLICATIONS

Rubine, D.H. (Dec. 1991). "The Automatic Recognition of Gestures," CMU-CS-91-202, Submitted in Partial Fulfillment of the Requirements for the Degree of Doctor of Philosophy in Computer Science at Carnegie Mellon University, 285 pages.

Rubine, D.H. (May 1992). "Combining Gestures and Direct Manipulation," CHI '92, pp. 659-660.

Shi, V. et al. (Jul. 20, 2009). "Non-contact Reflection Photoplethysmography Towards Effective Human Physiological Monitoring," Journal of Medical and Biomedical Engineering, 30(3), 161-167.

Westerman, W. (Spring 1999). "Hand Tracking, Finger Identification, and Chordic Manipulation on a Multi-Touch Surface," A Dissertation Submitted to the Faculty of the University of Delaware in Partial Fulfillment of the Requirements for the Degree of Doctor of Philosophy in Electrical Engineering, 364 pages.

\* cited by examiner

PPG SENSOR HAVING LIGHT ARRIVAL ANGLE CONTROL AT DETECTOR

CROSS-REFERENCE TO RELATED APPLICATIONS

This application is a continuation of U.S. patent application Ser. No. 15/274,918, filed Sep. 23, 2016, now U.S. Pat. No. 10,687,717, which claims priority to U.S. Provisional Patent Application No. 62/235,188, filed Sep. 30, 2015, the contents of which are hereby incorporated by reference as if fully disclosed herein.

FIELD

The present disclosure relates generally to wearable devices and methods for measuring a photoplethysmographic (PPG) signal. The wearable devices may include a PPG sensor array capable of receiving light at particular viewing angles associated with increased pulsatile signal, and thus a high perfusion index. Physiological parameters such as heart rate and oxygen saturation may be monitored using such wearable devices.

BACKGROUND

The present disclosure relates generally to wearable devices and methods for measuring a photoplethysmographic signal. Most soft tissue will transmit and reflect both visible and near-infrared radiation. Thus, if light is projected onto an area of skin and the reflected light detected after its interaction with the skin, blood, and other tissues, time varying changes in light absorbance can be observed. This time varying light absorbance signal (photoplethysmographic or "PPG" signal) may be affected by a number of factors, some of which include the optical properties of the tissues and blood at the measurement site, and the wavelength of the light source.

PPG signals may be used in applications such as heart rate and oxygen saturation determination, and are highly susceptible to motion noise caused by bulk body movements and internal tissue motion. Although forces created by bulk body movements can be detected by an accelerometer, flexion, for example, of the finger or hand can generate internal tissue forces within the wrist that, for a wrist-worn device, would not necessarily be detected by an accelerometer (e.g., flexion can occur while the limbs are stationary).

PPG signals may be also be affected by non-pulsatile signal artifacts. For a typical PPG detector (photodetector), the detector is sensitive to light arriving from all angles. However, some of the arrival angles include light containing more pulsatile signal than other angles. Perfusion index (PI) is a numerical assessment of pulse strength (pulse amplitude) at a monitoring site, and is generally the ratio of received modulated light to received unmodulated light at a photodetector or sensor. In a clinical setting, PI may be used to quickly evaluate the appropriateness of a sensor application site, where the site with the highest PI number is used. Placing the sensor at the site with a high PI may result in a higher quality PPG signal that is not contaminated with artifacts due to internal tissue motion or a non-pulsatile signal. However, it may not always be feasible to move or reposition a wearable device in order to find a favorable monitoring site. Accordingly, having new wearable devices and methods for measuring a PPG signal would be beneficial.

SUMMARY

Disclosed herein are wearable devices for obtaining physiological signals that include a PPG sensor array configured to receive reflected light at certain viewing angles associated with an increased PPG signal. The PPG signal generally refers to an optical signal based on the absorbance of light that can be used in various applications, e.g., heart rate and oxygen saturation ($SpO_2$) determination. As used herein the term "viewing angle" refers to the angle of light viewed by the detector. The PPG signal obtained at this preset viewing angle ($\Theta_{view}$) is generally associated with light containing a high level of pulsatile signal, and generally correlates with an optimal point ($\Theta_{PI,max}$), where perfusion index is high or at a maximum. The PPG signal obtained in this manner may be analyzed to provide a numerical value corresponding to a physiological parameter of an individual, e.g., the heart rate or oxygen saturation of a user.

In general, the wearable devices may include a housing structured for attachment to a body region of the individual, the housing comprising a PPG sensor array, the PPG sensor array comprising an illumination system and a detection system; and a processor within the housing configured to analyze a PPG signal obtained from the detection system and determine the physiological parameter. The illumination system may be configured to project light to a tissue layer within the body region, and the detection system may comprise a viewing component configured to receive light reflected from the tissue layer at a preset viewing angle. The preset viewing angle may be associated with a high level of pulsatile signal.

The illumination system may include at least one light emitter for projecting light to a tissue layer within a body region of an individual, and at least one photodetector for detecting light reflected by the tissue layer. As used herein, the terms "detector," "photodetector," and "PPG detector" are used interchangeably. It may be beneficial for the PPG sensor array to include a plurality of light emitters and a plurality of photodetectors.

Exemplary viewing components include without limitation, a plurality of slats and light tubes or pipes that have a preset viewing angle associated with a high level of pulsatile signal. It is understood that other viewing components may be employed with the PPG sensor array, so long as they are capable of controlling the angle of light received by the photodetector to a preset viewing angle.

Methods for obtaining a PPG signal and monitoring a physiological parameter of an individual are also disclosed herein. The methods generally include the steps of: securing a wearable device to a body region of the individual, the wearable device comprising a PPG sensor array, the PPG sensor array comprising an illumination system and a detection system; projecting light from the illumination system to a tissue layer within the body region; detecting light reflected from the tissue layer at a preset transmission angle that is associated with a PPG signal having a high level of pulsatile signal using the detection system; and analyzing the PPG signal to determine a physiological parameter, where the preset viewing angle is determined by a viewing component. The viewing component may be configured as a plurality of slats or light tubes or pipes, but is not so limited, as previously stated. The PPG signal may be analyzed to provide a numerical value corresponding to a physiological parameter of an individual, e.g., the heart rate or oxygen saturation, of a user.

The terminology used in the description of the various described embodiments herein is for the purpose of describing particular embodiments only and is not intended to be limiting. As used in the description of the various described embodiments and the appended claims, the singular forms "a", "an," and "the" are intended to include the plural forms as well, unless the context clearly indicates otherwise.

It will also be understood that the term "and/or" as used herein refers to and encompasses any and all possible combinations of one or more of the associated listed items. It will be further understood that the terms "includes," "including," "comprises," and/or "comprising," when used in this specification, specify the presence of stated features, integers, steps, operations, elements, and/or components, but do not preclude the presence or addition of one or more other features, integers, steps, operations, elements, components, and/or groups thereof.

DESCRIPTION OF THE FIGURES

For a better understanding of the various described embodiments, reference should be made to the Detailed Description below, in conjunction with the following drawings in which like reference numerals refer to corresponding parts throughout the figures.

DETAILED DESCRIPTION

Figure 1A:
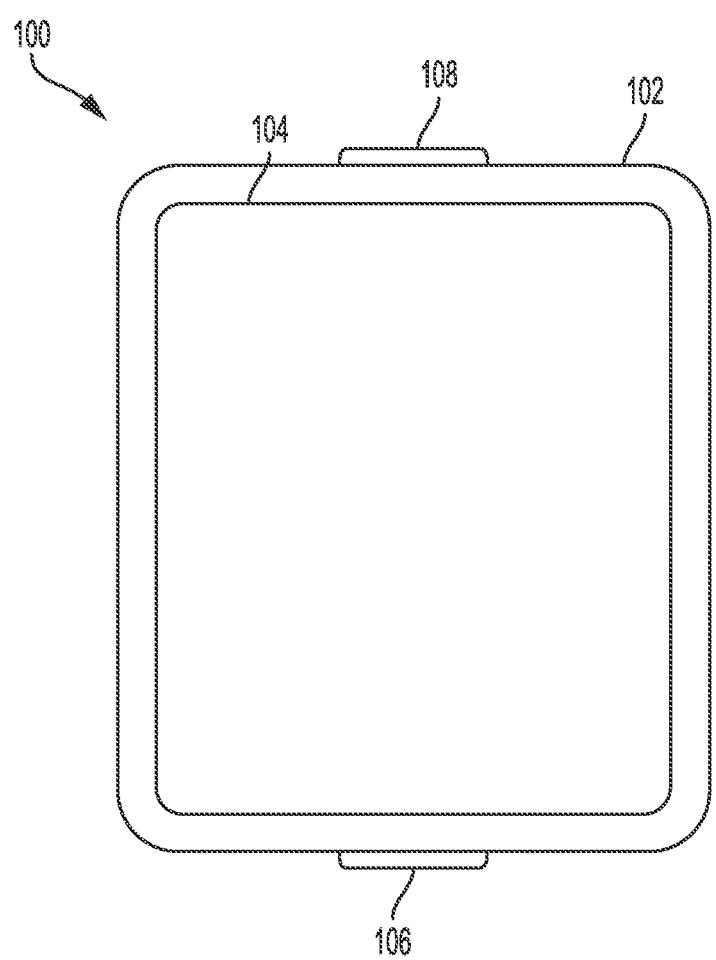
FIG. 1A depicts an exemplary wearable device.

The following description sets forth exemplary wearable devices and methods for measuring a PPG signal. It should be recognized, however, that such description is not intended as a limitation on the scope of the present disclosure but is instead provided as a description of exemplary embodiments.

The wearable devices described herein are capable of obtaining PPG signals by employing a PPG sensor array configured to control or preferentially accept light associated with a high level of pulsatile signal, which generally correlates to a high or maximum perfusion index value. The wearable devices may include a housing structured for attachment to a body region of the individual, the housing comprising a PPG sensor array, the PPG sensor array comprising an illumination system and a detection system; and a processor within the housing configured to analyze a PPG signal obtained from the detection system and determine the physiological parameter. The illumination system may be configured to project light to a tissue layer within the body region, and the detection system may comprise a viewing component configured to receive light reflected from the tissue layer at a preset viewing angle associated with a PPG signal having a high level of pulsatile signal. In some instances, the viewing component is also configured to block (or reduce passage of) light having a substantial amount of non-pulsatile signal artifact.

Some variations of the wearable devices comprise a housing having an upper surface, a back surface, and side surfaces; a PPG sensor array within the housing; and a processor within the housing configured to run an algorithm using information obtained from the PPG sensor array to determine a physiological parameter, e.g., heart rate, oxygen saturation, etc., of an individual. A viewing component coupled to the PPG sensor system and/or housing may facilitate the transmission of light to the photodetector at certain viewing angles that are associated with a high perfusion index. The light received at these viewing angles may be used to obtain PPG signals that may then be employed to provide data related to a user's heart rate or oxygen saturation.

The wearable device may be any electronic device suitable for contact with a body region of an individual, e.g., a user's skin, wrist, arm, leg, etc. Accordingly, the wearable device may be a phone, wristwatch, arm or wristband, headband, or any wearable device suitable for collecting PPG signals or biometric information. The wearable device may be worn on a wrist, ankle, head, chest, leg, etc., with the use of a band that is flexible and capable of adjustably fitting a user. For example, the band may be made from a flexible material or have a structure that allows it to have an adjustable circumference. In one variation, the wearable device is a wristwatch.

The housing of the wearable devices may be configured to have any size and shape suitable for the body region of contact, and may include a housing comprising an upper surface, a back surface, and side surfaces, an interior enclosed within the surfaces, and a display that is mounted in the upper surface of the housing. The display may, for example, be a touch screen that incorporates capacitive touch electrodes or may be a display that is not touch sensitive. The display may include image pixels formed from light-emitting diodes (LEDs), organic LEDs (OLEDs), plasma cells, electrowetting pixels, electrophoretic pixels, liquid crystal display (LCD) components, or other suitable image pixel structures.

In some variations, the wearable device is a device where operation of a predefined set of functions on the device is performed exclusively through a touch screen. By using a touch screen as the primary input control device for operation, the number of physical input control devices (such as push buttons, dials, and the like) on the wearable device may be reduced. The predefined set of functions that are performed exclusively through a touch screen optionally include navigation between user interfaces. In one variation, the touchpad, when touched by the user, navigates the wearable device to a main, home, or root menu from any user interface/mode that is displayed on device. In such variations, a "menu button" is implemented using a touch screen.

The display may include icons or other graphics that indicate various operating modes selectable by the user, e.g., heart rate mode, pedometer mode, etc. A graphics module included in the housing may employ various known software components for rendering and displaying graphics on the touch screen or other display, including components for changing the visual impact (e.g., brightness, transparency, saturation, contrast, or other visual property) of graphics that are displayed. As used herein, the term "graphics" includes any object that can be displayed to a user, including, without limitation, text, web pages, icons (such as user-interface objects including soft keys), digital images, videos, animations, and the like. In some variations, the graphics module stores data representing graphics to be used. Each graphic is, optionally, assigned a corresponding code. Here the graphics module receives, from applications etc., one or more codes specifying graphics to be displayed along with, if necessary, coordinate data and other graphic property data, and then generates screen image data to output to a display controller.

The housing, which may sometimes be referred to as a case, may be formed of plastic, glass, ceramics, fiber composites, metal (e.g., stainless steel, aluminum, etc.), other suitable materials, or a combination of these materials. In some variations, the housing or parts thereof may be formed from dielectric or other low-conductivity material. In other variations, the housing or at least some of the structures that make up the housing may be formed from metal elements.

A display cover layer such as a layer of cover glass or a transparent plastic layer may cover the surface of display. The display cover layer may have one or more openings. Windows may be provided in the display cover layer to allow light to pass through the display cover layer in connection with the operation of a light sensor, camera, or other optical component.

Referring to FIG. 1A, an exemplary wearable device (100) is shown. In brief, device (100) includes a housing (102) and touch-sensitive display screen (104), hereafter touch screen (104). Alternatively, or in addition to touch screen (104), device (100) has a display and a touch-sensitive surface. Touch screen (104) (or the touch-sensitive surface) may have one or more intensity sensors for detecting intensity of contacts (e.g., touches) being applied. The one or more intensity sensors of touch screen (104) (or the touch-sensitive surface) can provide output data that represents the intensity of touches. The user interface of device (100) can respond to touches based on their intensity, meaning that touches of different intensities can invoke different user interface operations on device (100).

In some variations, device (100) has one or more input mechanisms (106) and (108). Input mechanisms (106) and (108), if included, can be physical. Examples of physical input mechanisms include push buttons and rotatable mechanisms. Device (100) may have one or more attachment mechanisms. Such attachment mechanisms, if included, can permit attachment of device (100) with, for example, hats, headbands, eyewear, clothing, watch straps, belts, shoes, and so forth. These attachment mechanisms may permit device (100) to be worn by an individual. Exemplary attachment mechanisms include without limitation, bands that may be secured to the user through the use of hooks and loops (e.g., Velcro), a clasp, and/or a band having memory of its shape, e.g., through the use of a spring metal band.

Figure 1B:
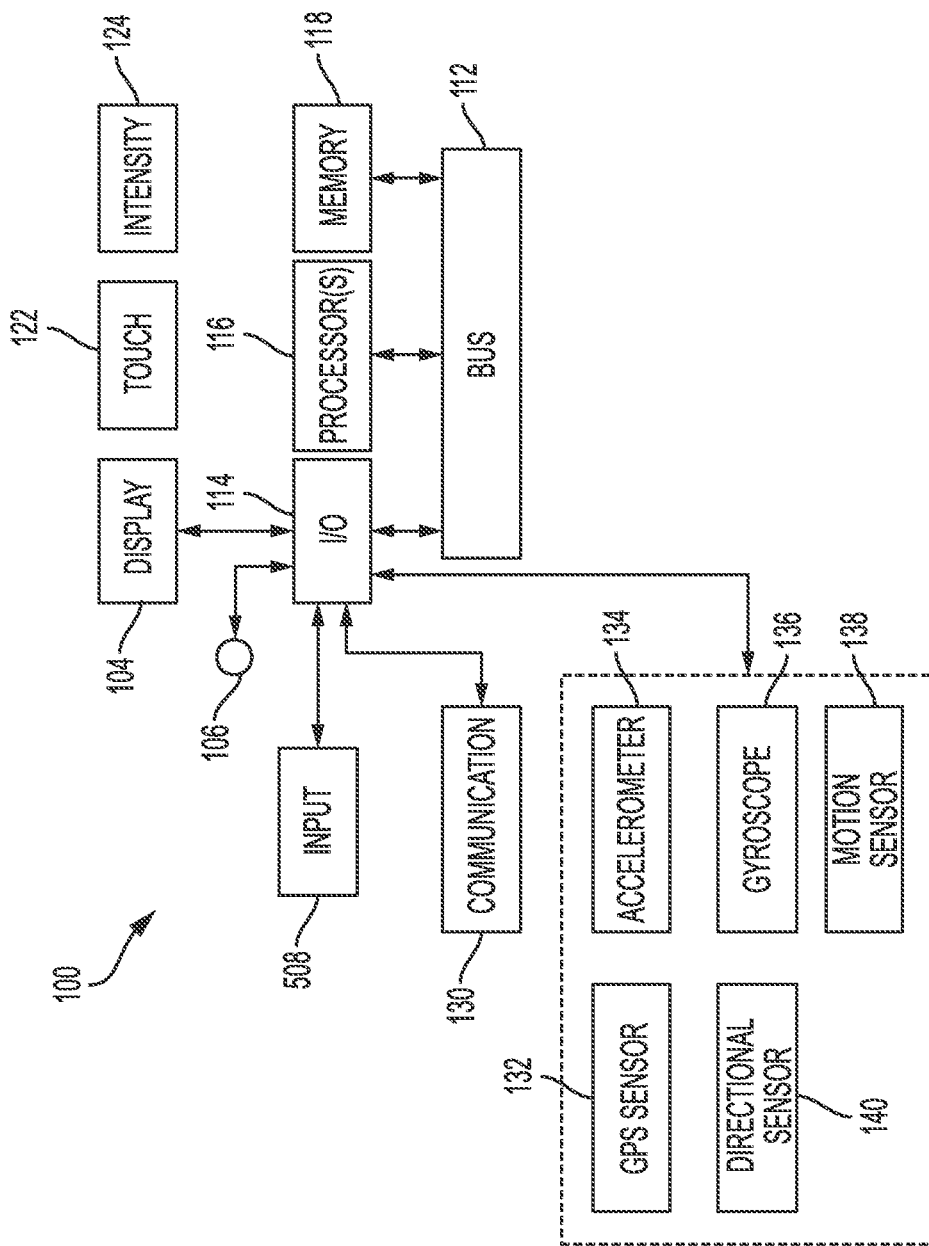
FIG. 1B is a block diagram showing the components of the wearable device in FIG. 1A.

FIG. 1B provides further details on the components of wearable device (100). Here device (100) has bus (112) that operatively couples I/O section (114) with one or more computer processors (116) and memory (118). I/O section (114) can be connected to display (104), which can have touch-sensitive component (122) and, optionally, touch-intensity sensitive component (124). In addition, I/O section (114) can be connected with communication unit (130) for receiving application and operating system data, using Wi-Fi, Bluetooth, near field communication (NFC), cellular, and/or other wireless communication techniques.

The wearable device (100) can also include various sensors, such as GPS sensor (132), accelerometer (134), directional sensor (140) (e.g., compass), gyroscope (136), motion sensor (138), sensors for detecting various types of physiological information, e.g., temperature, and/or a combination thereof, all of which can be operatively connected to I/O section (114).

Memory (118) of wearable device (100) can be a non-transitory computer-readable storage medium, for storing computer-executable instructions, which, when executed by one or more computer processors (116), for example, can cause the computer processors to perform the algorithms further described below. The computer-executable instructions can also be stored and/or transported within any non-transitory computer-readable storage medium for use by or in connection with an instruction execution system, apparatus, or device, such as a computer-based system, processor-containing system, or other system that can fetch the instructions from the instruction execution system, apparatus, or device and execute the instructions. For purposes of this document, a "non-transitory computer-readable storage medium" can be any medium that can tangibly contain or store computer-executable instructions for use by or in connection with the instruction execution system, apparatus, or device. The non-transitory computer-readable storage medium can include, but is not limited to, magnetic, optical, and/or semiconductor storages. A processor (not shown) may be included in the housing that is configured to run various algorithms based on information obtained from the PPG sensor array, e.g., the detection system. It is understood that wearable device (100) is not limited to the components and configuration of FIGS. 1A and 1B, but can include other or additional components in multiple configurations.

The wearable devices may include a PPG sensor array, as previously stated. The PPG sensor array generally comprises at least one light emitter and at least one photodetector. A PPG signal (derived from the amount of light reflected after interaction with a skin layer) obtained from light received by a viewing component of the PPG sensor array can be processed to obtain physiological information (e.g., heart rate, oxygen saturation, etc.). In basic form, the PPG sensor array can employ a light source or light emitter that injects light into the user's tissue and a light detector (photodetector) to receive light that reflects and/or scatters and exits the tissue. The PPG signal is typically the amplitude of the reflected and/or scattered light that is modulated with volumetric change in blood volume in the tissue. Exemplary light emitters include without limitation, light emitting diodes (LEDs), incandescent lights, and fluorescent lights. The LED may be a green LED, red LED, or an infrared (IR) LED. When more than one light emitter is used, the plurality can include the same or different light emitters (with different emission wavelengths). For example, a combination of one or more green LEDs and IR LEDs may be used. In some variations, the light emitting diodes emit light with a peak spectral response between about 400 and 620 nm.

The PPG sensor array may be provided in any suitable location on the wearable device. In one variation, the housing of the wearable device comprises the PPG sensor system. For example, the system may be disposed on the back housing surface. In some variations, the light emitters of a PPG sensor array may be provided on a combination of surfaces, e.g., the back surface and a side surface of the wearable device housing. One or more light emitters can be provided on an attachment mechanism of the wearable device. For example, when the wearable device is a wristwatch, one or more of the light emitters can be disposed on the wristband.

The photodetectors may also be provided and arranged in any suitable location(s) on the wearable device. In one variation, one or more photodetectors are disposed on the back surface of the wearable device housing. In another variation, one or more photodetectors are disposed on a side surface of the wearable device housing. Photodetectors may also be provided on a combination of surfaces, e.g., the back surface and a side surface of the wearable device housing. One or more photodetectors can be provided on an attachment mechanism of the wearable device. For example, when the wearable device is a wristwatch, one or more of the photodetectors can be disposed on the wristband. The photodetector typically generates an electrical current that is proportional to the amount of light detected. Another detector may be provided to convert the electrical current from the photodetector to a voltage that is proportional to the current.

The light emitter(s) may emit light having one or more wavelengths that are specific or directed to a type of physiological data to be collected. In one variation, the light emitter(s) emit light having one or more wavelengths specific to the collection of PPG signals. Similarly, the photodetectors may sample, measure and/or detect one or more wavelengths that are also specific or directed to a type of physiological data to be collected. For instance, a light source emitting light having a wavelength in the green spectrum and a photodiode positioned to detect a response or reflection corresponding with such light may provide data that may be used to determine, e.g., heart rate and oxygen saturation.

The PPG signal may be compromised by noise due to artifacts. As previously stated, PPG sensor systems are generally designed to be sensitive to blood volume modulation in tissue in order to derive corresponding physiological signals, e.g., heart rate and oxygen saturation. Such systems generally include a light emitter that injects light into tissue, and a photodetector to receive light that exits the tissue. The signal of interest, e.g., the PPG signal, is an optical signal that relates to differences in the absorbance of light after interaction with tissue, blood, etc.

A typical photodetector system is sensitive to light arriving from all arrival angles, e.g., light including non-pulsatile signal artifacts and light including pulsatile signals. Given that skin is comprised of various layers, and that only some of these layers, e.g., the dermis or dermal layer, comprise blood vessels, light arriving from some of these angles contains non-pulsatile signal noise. Accordingly, various viewing components can be included with the wearable devices that are configured to improve the PPG signal by substantially receiving light reflected from a tissue layer containing blood vessels. In general, the viewing component is structured to receive light reflected at certain viewing angles associated with reflection from a pulsatile signal tissue layer, and thus, a high or maximum perfusion index.

The viewing component may be coupled to a portion of the wearable device housing or a portion of the PPG sensor array, e.g., the photodetector.

Figure 2:
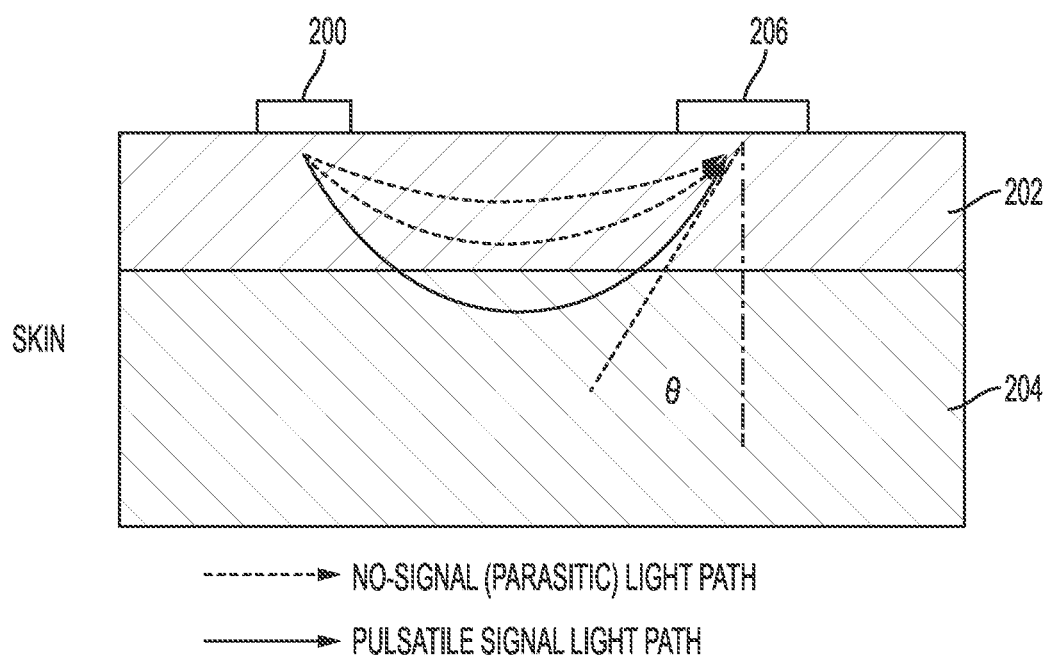
FIG. 2 depicts an exemplary PPG sensor system where the photodetector receives light containing both pulsatile signal and non-pulsatile signal artifact.
Figure 3:
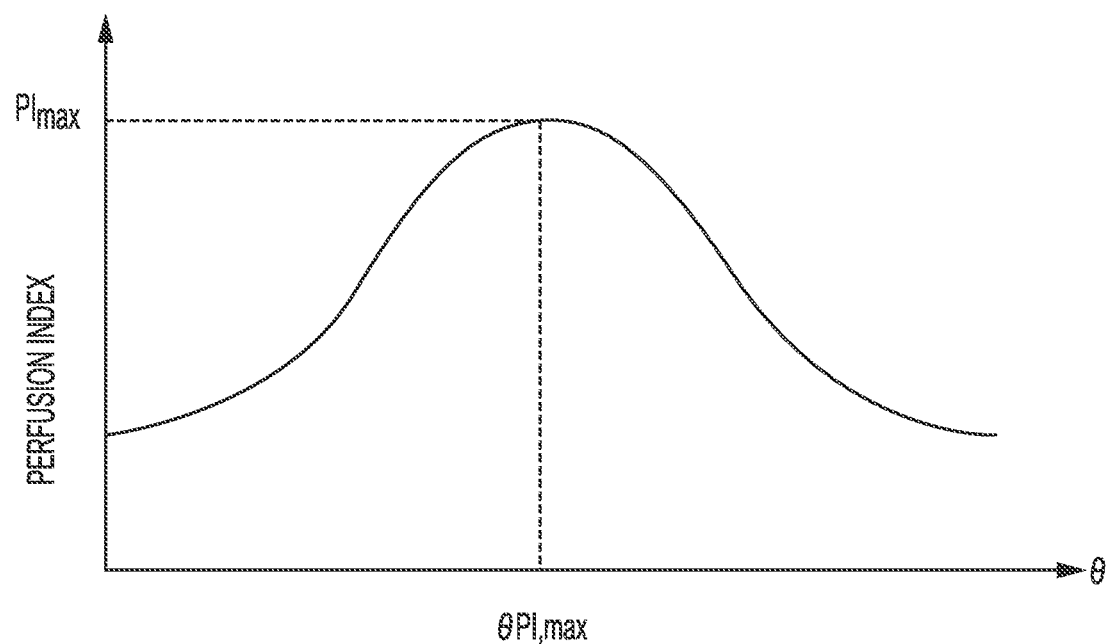
FIG. 3 illustrates how light received at an optimal point ($\Theta_{PI,max}$) is associated with a high or maximum perfusion index.

For example, and as shown in FIG. 2, light emitted from a LED (200) travels through both the epidermis (202) and the dermis (204) of the skin. Light travelling through the epidermis (202) and received at the photodetector (206) contains no (or a low level) of pulsatile signal since that skin layer typically does not include blood vessels. However, light traveling through the dermis (204) and received at an angle ($\Theta$) by the photodetector (206) contains pulsatile signal given that the dermis (204) typically includes blood vessels. Thus, to improve the quality of the PPG signal sensed by photodetector (206) it would be beneficial to block or mitigate light arriving from the non-pulsatile signal layer (i.e., non-pulsatile signal noise) at the photodetector (206), and receive light arriving from the dermis (204) (pulsatile signal layer) at an optimal point/angle where perfusion index is high or at a maximum. As shown in FIG. 3, perfusion index (PI) (i.e., the ratio of received modulated and unmodulated light) is not uniformly distributed over all light arrival angles ($\Theta$), but has an optimal point ($\Theta_{PI,max}$) where PI is at a maximum ($PI_{max}$).

The viewing component generally enables the photodetector to receive or accept light at the preset viewing angle (i.e., the optimal point ($\Theta_{PI,max}$)). To reiterate, light received at an optimal point ($\Theta_{PI,max}$) is generally correlated with a maximum PI ($PI_{max}$), and typically includes a high level of pulsatile signal. Thus, any viewing component configured to control the viewing angle of the photodetector to preferentially transfer, receive, or accept light at an optimal point ($\Theta_{PI,max}$) may be employed in the wearable devices disclosed herein. In other words, it would be beneficial to have a viewing component that enables the photodetector to have a viewing angle ($\Theta_{view}$) equal to about $\Theta_{PI,max}$. Additionally or alternatively, the viewing component may be used to mitigate light paths associated with ambient light intrusion.

One or more viewing components can be provided with the wearable devices. The one or more viewing components will generally be coupled to the photodetector of the PPG sensor array. When a plurality of viewing components is employed, they may be the same or different viewing components. Additionally, each one of the plurality of viewing components can have a unique viewing angle, or the plurality of viewing components can have the same viewing angle. The viewing component may be made from any suitable material such as polymers or metals. In one variation, the viewing component can be attached to the photodetector using conventional methods, e.g., by the use of adhesives, welding, etc.

Figure 4:
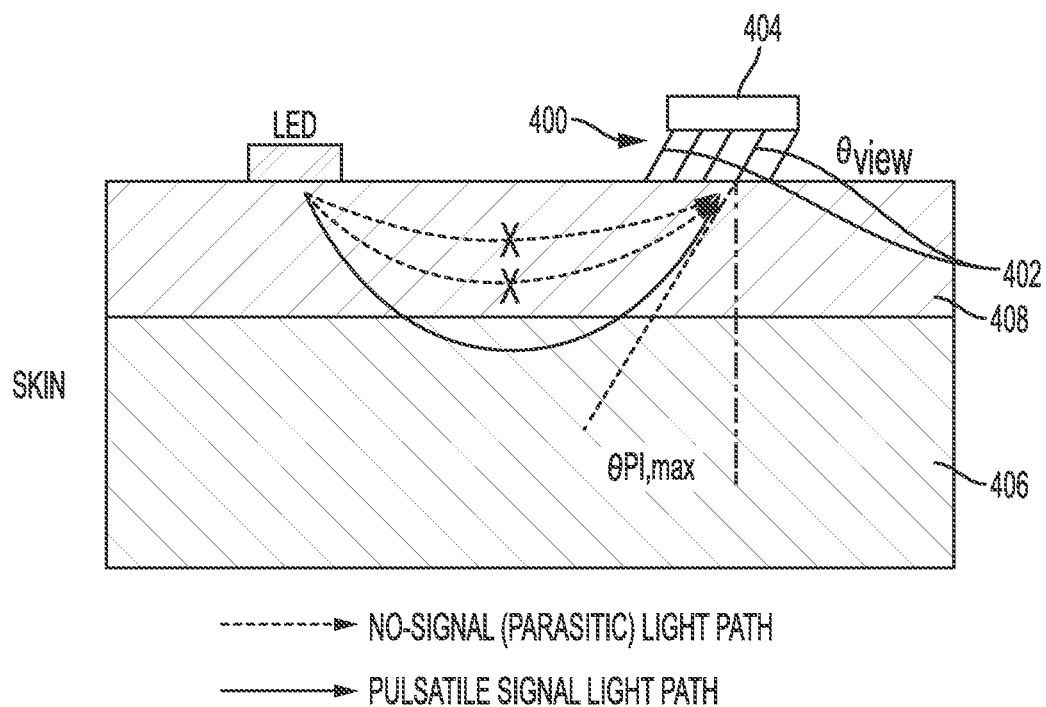
FIG. 4 depicts an exemplary PPG sensor array having a viewing component according to one variation that enables the photodetector to receive light arriving at an optimal point ($\Theta_{PI,max}$) and block light arriving from a non-pulsatile signal skin layer.

In some variations, the channeling component comprises a plurality of slats angled to allow light to be received at viewing angles associated with a high level of pulsatile signal, and block light travelling at other angles to the photodetector. The slats may be made from the materials mentioned above, and may have any suitable length and width. The slats may be disposed over the entire area of the photodetector or a portion thereof. The slats may be grouped together or spaced upon the photodetector(s) in any suitable configuration. When more than one photodetector is included in the PPG sensor array, each photodetector can be coupled to viewing structures with slats having the same or different viewing angles. Referring to FIG. 4, a viewing component (400) comprising a plurality of slats (402) is shown. Viewing component (400) is disposed over the entire area of photodetector (404). The slats (402) are angled with respect to the photodetector (404) so that the photodetector has a viewing angle ($\Theta_{view}$) equal to about $\Theta_{PI,max}$. Accordingly, light received from the pulsatile signal layer (406) is viewed by the photodetector while light arriving from the non-pulsatile signal layer (408) is blocked.

Figure 5:
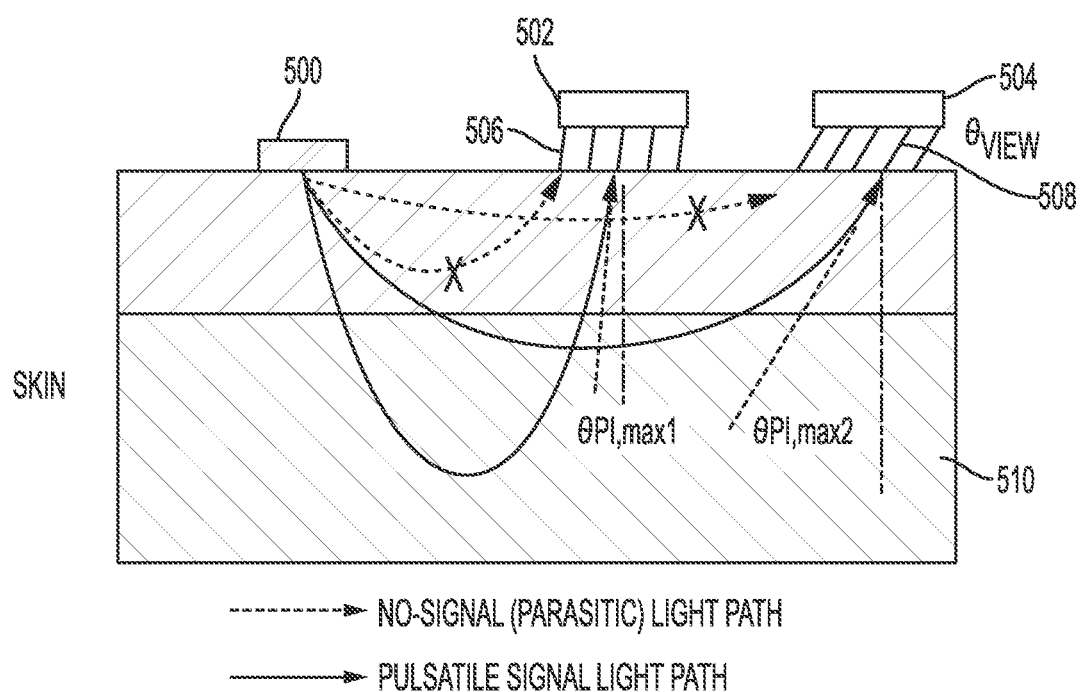
FIG. 5 depicts an exemplary PPG sensor array having a viewing component according to another variation.

When a plurality of photodetectors is used in the PPG sensor array, the light emitter-photodetector pair or other combination (e.g., one or more light emitters and a photodetector array) can be spaced and/or positioned on the wearable device to create a specific viewing angle or $\Theta_{PI,max}$. In this manner, detection by the photodetectors can be better tailored to the signal of interest. Furthermore, travel of the light into deeper tissues where internal tissue motion occurs can be avoided. For example, as shown in FIG. 5, the PPG sensor array includes a single LED (500) and two photodetectors P1 (502) and P2 (504), which are spaced different distances from the LED (500). P1 (502) and P2 (504) are also coupled to viewing components comprising a plurality of slats (506 for P1 and 508 for P2) that provide a unique viewing angle or $\Theta_{PI,max}$ for each photodetector. The $\Theta_{PI,max}$ for P1 (502) is shown as $\Theta_{PI,max1}$, and the $\Theta_{PI,max}$ P2 (504) is indicated as $\Theta_{PI,max2}$. P1 (502), which is closer to LED (500) is capable of receiving light from a deeper part of the pulsatile signal layer (510) that also has a viewing angle equal to about $\Theta_{PI,max1}$. As shown in the figure, light arriving at other angles at P1 (502) are blocked by the slats (506). Likewise, P2 (504), which is spaced further from LED (500) is capable of receiving light from a different and more superficial part of the pulsatile signal layer (510) that also has a viewing angle equal to about $\Theta_{PI,max2}$. Light arriving at other angles at P2 (504) are blocked by slats (508).

Figure 6A:
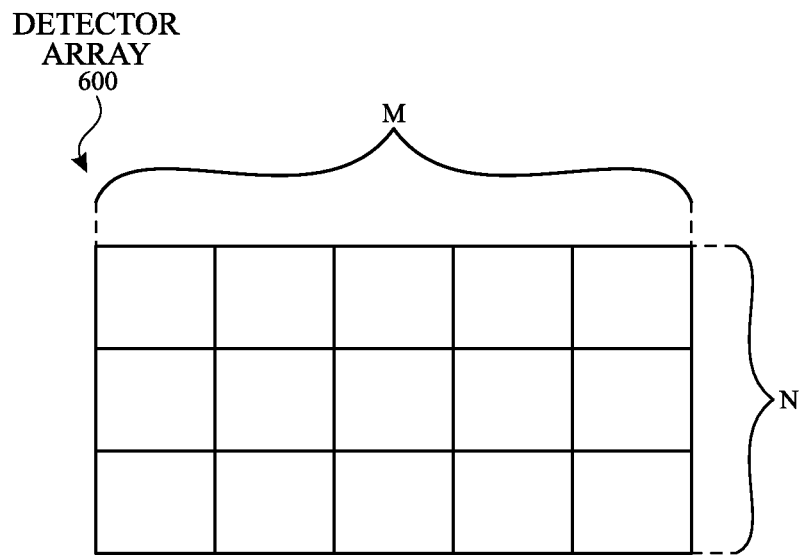
FIG. 6A illustrates an exemplary detector array according to examples of the disclosure.

In some examples, the plurality of photodetectors can be arranged as a detector array configured to measure a variety of viewing angles of light reflected from the same tissue region. FIG. 6A illustrates an exemplary detector array according to examples of the disclosure. Detector array 600 can include a plurality of detectors arranged in n rows and m columns (i.e., m×n detector array). Each detector included in detector array 600 can be configured with a different viewing angle. Additionally, each detector can be configured with a different separation distance from the light source (not shown).

In some examples, the controller can accept, reject, or scale each signal according to one or more characteristics of the signal. For example, the controller can acquire signals from all the detectors in detector array 620. Three signals with the highest SNR that are associated with a given wavelength range can be processed and used in determining the physiological parameters.

Figure 6B:
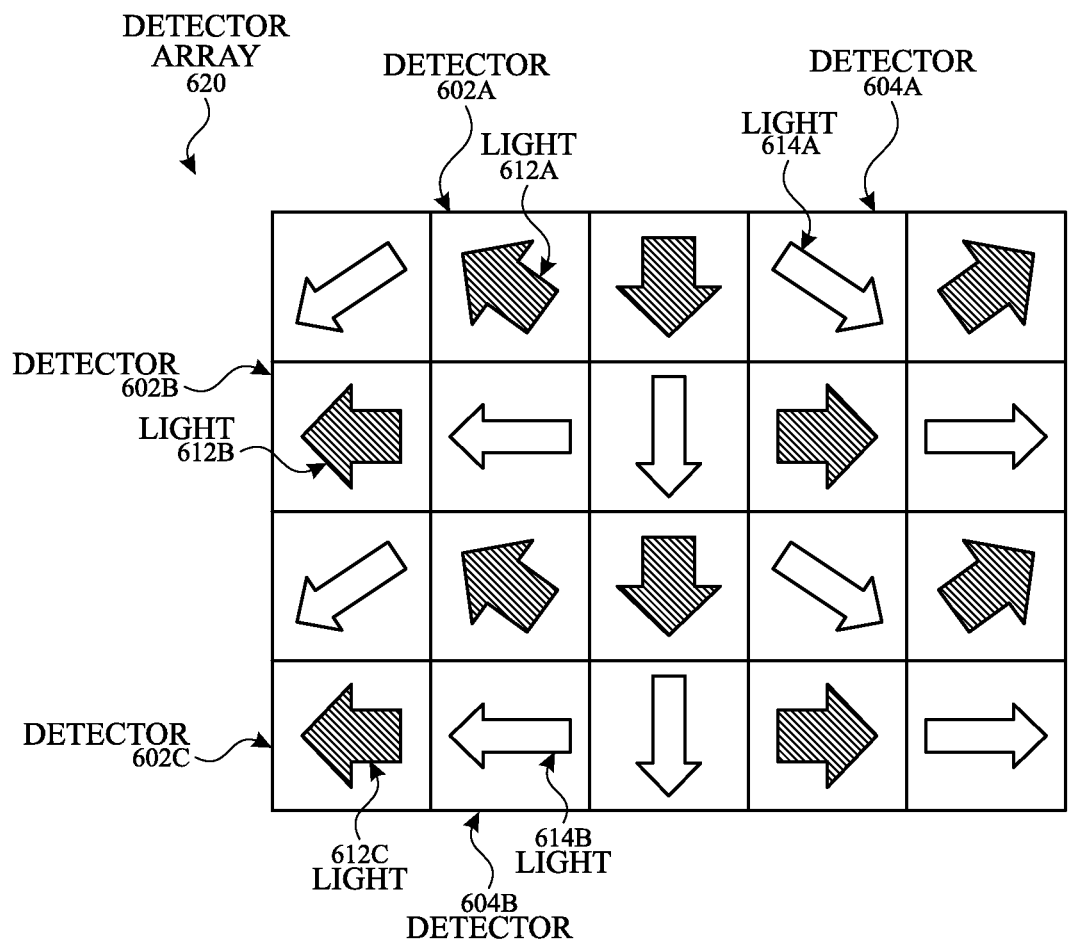
FIG. 6B illustrates a detector array used to measure the same tissue region according to examples of the disclosure.

In some examples, the plurality of photodetectors can be arranged as a detector array configured to measure the same region, but different layers (e.g., depths) of tissue. FIG. 6B illustrates a detector array used to measure the same tissue region according to examples of the disclosure. Detector array 620 can include a plurality of detectors, such as detectors 602a, 602b, 602c, 604a, and 604b. Detectors 602a, 602b, and 602c can be configured to detect light 612a, 612b, and 612c, respectively. Light 612a, 612b, and 612c can include one or more first wavelengths (e.g., visible, such as green, wavelengths). Detectors 604a and 604b can be configured to detect light 614a and 614b, respectively. Light 614a and 614b can include one or more second wavelengths (e.g., infrared wavelengths). In some examples, the one or more first wavelengths can be separate and distinct from the one or more second wavelengths. Detector array 620 can be configured to detect the different wavelengths of light, and the controller can process the signals having different depths of penetration into the skin tissue. For example, light 614a and 614b can be absorbed by deeper tissue layers than light 612a, 612b, and 612c. For a given wavelength range (e.g., the one or more first wavelengths), light with different viewing angles can be measured. For example, light 612a can have a first viewing angle and light 612b can have a second viewing angle.

In some examples, light (e.g., light 612b and 612c) with the same viewing angle can be measured, but can have different separation distances from the light source (e.g., LED 500 illustrated in FIG. 5). Although the separation distances of, for example, detector 602b and 602c, can differ, the detectors included in detector array 620 can be located close enough such that the same tissue region can be measured. Variations in the separation distance can lead to variations in the pitch of the viewing angles. Narrow viewing angles can spread when the separation distance increases, and wide viewing angles can spread when the separation distance decreases. In this manner, a total range of viewing angles can be measured. Each detector in detector array 620 can be configured to measure a subset of the total range of viewing angles, which can allow the controller to associate different signals to different viewing angle(s). The controller can selectively acquire, process, and/or scale each signal according its associated viewing angle(s).

Examples of the disclosure can include one or more detectors can be configured to measure light with different wavelengths, the same separation distance, and different viewing angles. For example, detector 602b can be configured to measure different wavelengths (e.g., visible and infrared wavelengths) and can be coupled to different viewing components (e.g., one viewing component configured with slats 506 and another viewing component configured with slats 508 illustrated in FIG. 5). In some examples, one or more detectors can be configured to measure light with different wavelengths, different separation distances, and the same viewing angle. For example, light 612c and light 614b can have different wavelengths, but the same viewing angle; and detector 602c and detector 604b can have different separation distances.

Figure 7:
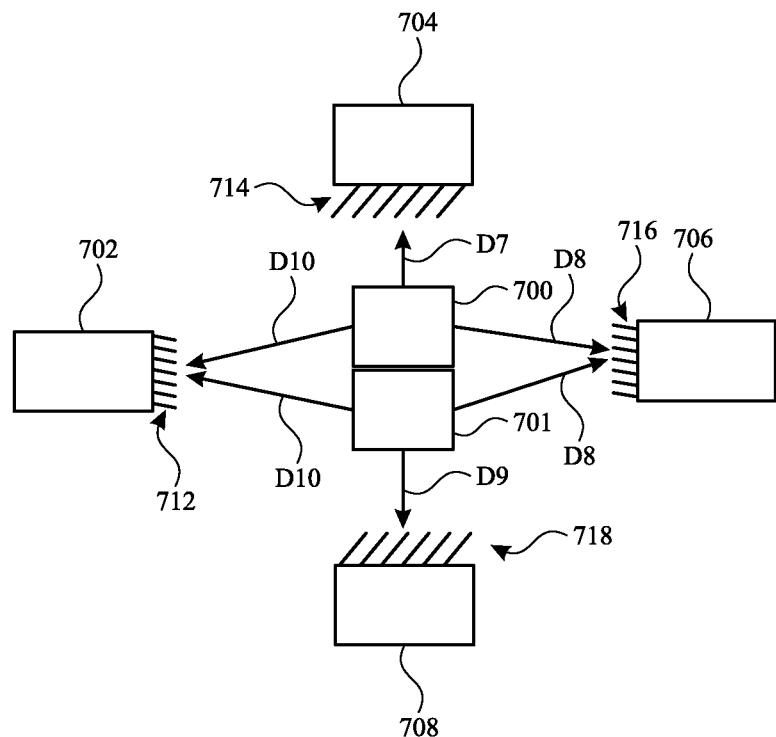
FIG. 7 illustrates an exemplary PPG sensor array according to examples of the disclosure.

In some examples, the PPG sensor array can be configured with a combination of the same and different wavelengths of light, the same and different separation distances, and the same and different viewing angles. FIG. 7 illustrates an exemplary PPG sensor array according to examples of the disclosure. The PPG sensor array can include a plurality of LEDs, such as LED 700 and LED 701, and a plurality of photodetectors, such as photodetectors 702, 704, 706, and 708. LED 700 and LED 701 can be configured to measure emit wavelengths of light. For example, LED 700 can be configured to emit infrared wavelengths, while LED 701 can be configured to emit green wavelengths. Photodetector 704 can be configured to measure light emitted by LED 700, and photodetector 708 can be configured to measure light emitted by LED 701. Photodetectors 702 and 706 can be configured to measure light emitted by both LED 700 and LED 701. Photodetector 702 can be located a separation distance d10 from LED 700 and LED 701; photodetector 704 can be located a separation distance d7 from LED 700; photodetector 706 can be located a separation distance d8 from LED 700 and LED 701; and photodetector 708 can be located a separation distance d9 from LED 701. In some examples, separation distance d8 can be the same as separation distance d10. In some examples, separation distance d7 can be different from separation distance d9. Additionally or alternatively, separation distance d8 (or separation distance d10) can be different from separation distance d7 (and/or separation distance d9).

A viewing component can be coupled to each photodetector. Viewing component 712 can be coupled to photodetector 702. Viewing component 714 can be coupled to photodetector 704. Viewing component 706 can be coupled to photodetector 716. Viewing component 718 can be coupled to photodetector 708. In some examples, viewing component 714 can be configured with the same viewing angle(s) as viewing component 718. In some examples, viewing component 712 can be configured with different viewing angles than viewing component 716. Additionally or alternatively, the viewing angles for viewing component 714 (or viewing component 718) can be different from the viewing angles for viewing component 712 (and/or viewing component 716).

In this manner, at least two measurements (e.g., photodetectors 702 and 704 measuring light emitted by LED 700) can include the same wavelength of light, while at least two measurements (e.g., photodetector 702 measuring light emitted by LED 700 and light emitted by LED 701) can include different wavelengths of light. At least two measurements (e.g., photodetector 702 and photodetector 706 measuring light emitted by LED 700 and/or LED 701) can have the same separation distance (between photodetector and light source), while at least two measurements (e.g., photodetector 704 measuring light emitted by LED 700, and photodetector 708 measuring light emitted by LED 701) can have different separation distances. At least two measurements (e.g., photodetector 704 measuring light emitted by LED 700, and photodetector 708 measuring light emitted by LED 701) can include the same viewing angles, while at least two measurements (e.g., photodetectors 702 and 706 measuring light emitted by LED 700 and/or LED 701) can include different viewing angles. Some or all of the plurality of measurements can be included for accurate determination of one or more physiological parameters.

Figure 8:
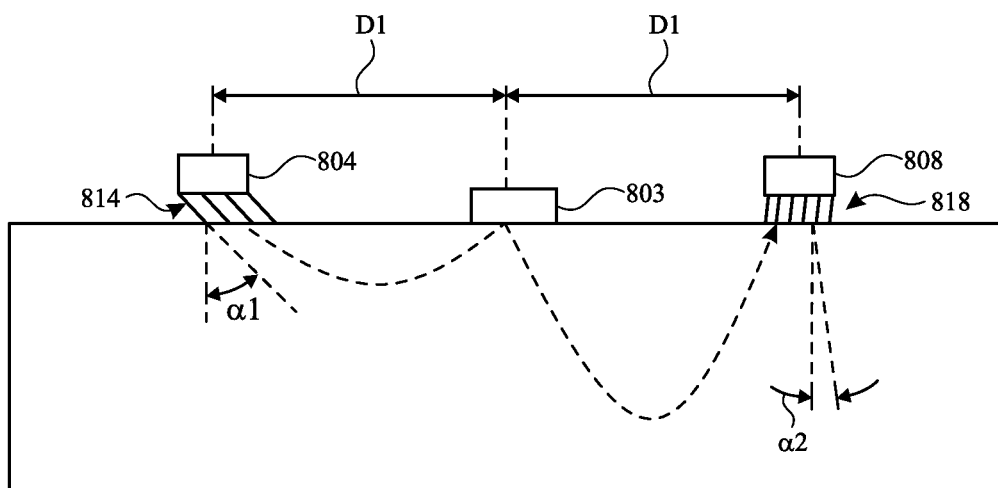
FIG. 8 illustrates an exemplary PPG sensor array according to examples of the disclosure.

In some examples, the PPG sensor array can be capable of accounting for different scattering profiles in the skin due to differences in, e.g., skin pigmentation. FIG. 8 illustrates an exemplary PPG sensor array according to examples of the disclosure. The PPG sensor array can include LED 803 and photodetectors 804 and 808. Photodetectors 804 and 808 can have the same separation distance dl from LED 803. Photodetector 804 can be coupled to viewing component 814, and photodetector 808 can be coupled to viewing component 818. In some examples, viewing component 814 can be configured with different viewing angle(s) $\alpha_1$ than the viewing angle(s) $\alpha_2$ of viewing component 818. Photodetector 808 and viewing component 818 can measure a different depth than photodetector 804 and viewing component 814. The controller can evaluate the strength of physiological signal (e.g., using frequency spectrum analysis like FFT) to select one or both signals for processing. Based on the selection, in some examples, the controller can continue to use the selected photodetector(s) for subsequent measurements.

Figure 9:
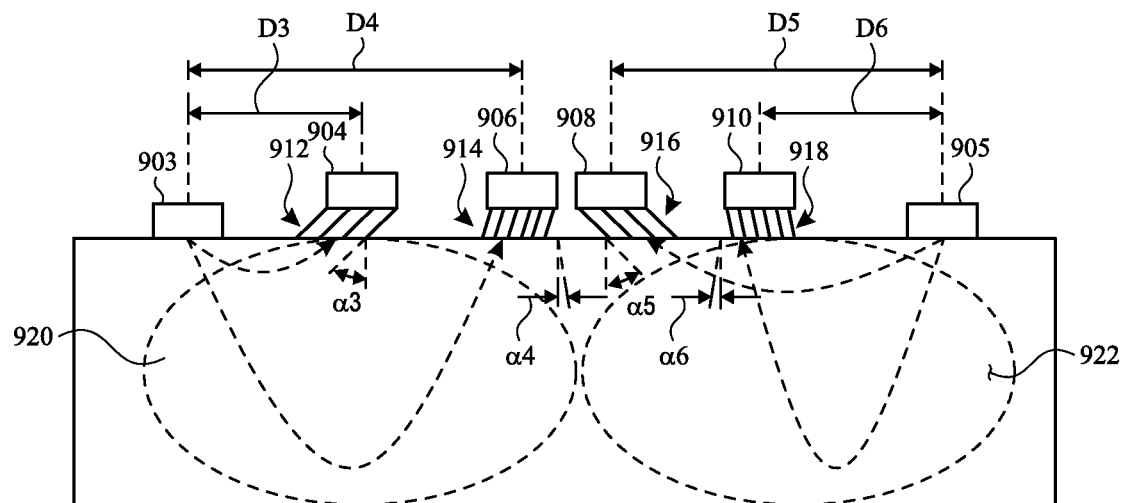
FIG. 9 illustrates an exemplary PPG sensor array according to examples of the disclosure.

In some examples, the PPG sensor can be capable of measuring different regions of skin tissue. FIG. 9 illustrates an exemplary PPG sensor array according to examples of the disclosure. The PPG sensor array can include LED 903 and LED 905 configured to interact with two different regions such as regions 920 and 922, respectively. The PPG sensor array can also include photodetectors 904, 906, 908, and 910. Photodetectors 904 and 906 can be optically coupled to LED 903 and can be configured to interact with region 920 of skin tissue. Photodetector 904 can be located a separation distance d3 away from LED 903, and photodetector 906 can be located a separation distance d4 away from LED 903, where separation distance d4 can be greater than separation distance d3. Photodetector 908 and 910 can be optically coupled to LED 905 and can be configured to interact with region 922 of skin tissue. Photodetector 910 can be located a separation distance d6 away from LED 905, and photodetector 908 can be located a separation distance d5 away from LED 905, where separation distance d5 can be greater than separation distance d6. In some examples, separation distance d4 and separation distance d5 can be the same. In some examples, separation distance d3 and separation distance d6 can be the same.

Each photodetector can be coupled to a viewing component. Photodetector 904 can be coupled to viewing component 912, which can have a viewing angle $\alpha_3$. Photodetector 906 can be coupled to viewing component 914, which can have a viewing angle $\alpha_4$. Photodetector 908 can be coupled to viewing component 916, which can have a viewing angle $\alpha_5$. Photodetector 918 can be coupled to viewing component 910, which can have a viewing angle $\alpha_6$.

Some of the viewing components can be configured with the same viewing angles, but can interact with different regions of skin tissue. For example, viewing angle $\alpha_3$ can be the same as viewing angle $\alpha_5$, but viewing component 912 (having viewing angle $\alpha_3$) and photodetector 904 can be associated with region 920 while viewing component 916 (having viewing angle $\alpha_5$) and photodetector 908 can be associated with region 922. Viewing angle $\alpha_4$ can be the same as viewing angle $\alpha_6$, but viewing component 914 (having viewing angle $\alpha_4$) and photodetector 906 can be associated with region 920 while viewing component 910 (having viewing angle $\alpha_6$) and photodetector 910 can be associated with region 922. In this manner, if the separation distances (e.g., separation distance d3 and separation d6) are the same, redundancy can be built in such that data is collected from different regions of skin tissue. If there is poor perfusion or SNR (e.g., due to skin pigmentation) in region 920, for example, but good perfusion in region 922, then the PPG sensor array can be configured to process measurements from region 922 or more favorably weigh measurements from region 922.

In some examples, some of the viewing components can be configured with different viewing angles, but can interact with the same region of skin tissue. For example, viewing angle $\alpha_3$ can be different from viewing angle $\alpha_4$, but both viewing component 912 (having viewing angle $\alpha_3$) and viewing component 914 (having viewing angle $\alpha_4$) can be associated with region 920. Similarly, viewing angle $\alpha_5$ can be different from viewing angle $\alpha_6$, but both viewing component 916 (having viewing angle $\alpha_5$) and viewing component 918 (having viewing angle $\alpha_6$) can be associated with region 922.

Figure 10:
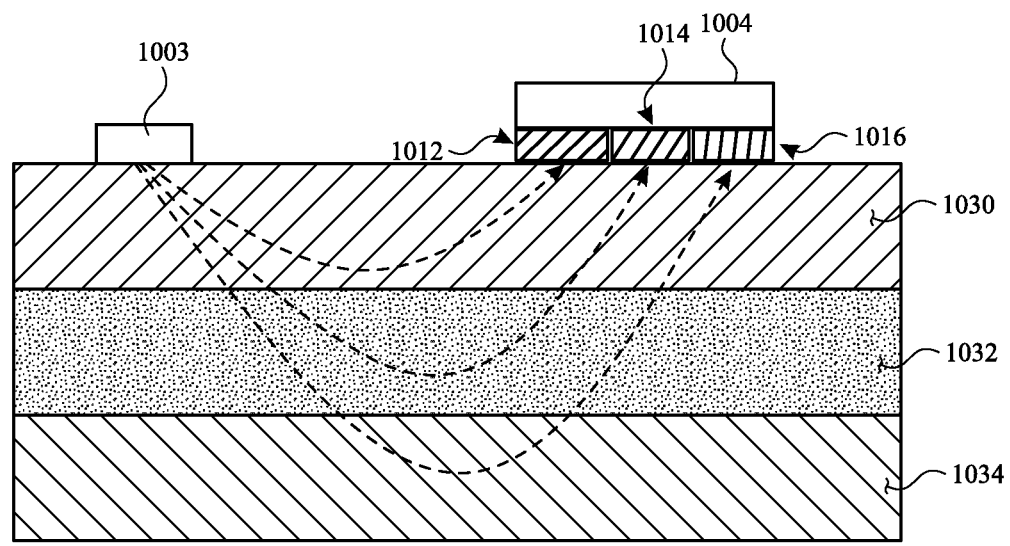
FIG. 10 illustrates an exemplary PPG sensor array according to examples of the disclosure.

In some examples, the PPG sensor array can be configured to have multiple different separation distances such that information from different depths of skin tissue can be obtained. For example, separation distances d3, d4, d5, and d6 can be different and four different depths (instead of two) can be measured. Examples of the disclosure can include LED 903 and LED 905 configured to emit either the same wavelength(s) of light or different wavelength(s) of light. In some examples, the PPG sensor array can include at least one signal detector coupled to one or more viewing components having a plurality of viewing angles. FIG. 10 illustrates an exemplary PPG sensor array according to examples of the disclosure. The PPG sensor array can include LED 1003 and photodetector 1004. Photodetector

1004 can be a single detector coupled to a plurality of viewing components such as viewing component 1012, viewing component 1014, and viewing component 1016. In some examples, photodetector 1004 can be a pixel-based detector array, where each viewing component can be coupled to a different pixel. Each viewing component coupled to the same detector can be configured with different viewing angles, which can allow the PPG sensor array the capability of measuring different depths and/or tissue layers. For example, viewing component 1012 can be configured to measure light that interacted with layer 1030, while rejecting light that has interacted with layers 1032 and 1034. Viewing component 1014 can be configured to measure light that interacted with layer 1032, while rejecting light that interacted with layers 1030 and 1034. Viewing component 1016 can be configured to measure light that interacted with layer 1034, while rejecting light that interacted with layers 1030 and 1032. A controller can associate each detector pixel with a certain layer of the skin tissue. In some examples, viewing components (e.g., viewing component 1012) closer to LED 1003 can have the larger viewing angles (e.g., 35°), while viewing components (e.g., viewing component 1016) further from LED 1003 can have viewing angles closer to normal incidence (e.g., 80°).

Some variations of the viewing component comprise light tubes (or light pipes) angled to allow light to be received at viewing angles associated with a high level of pulsatile signal, and block light travelling at other angles to the photodetector. The light tubes are generally sized for use in a wearable PPG sensor array, e.g., a wristwatch. One or more light tubes may be coupled to the PPG sensor array, typically to the photodetector. In one variation, one light tube may be coupled to a single photodetector. In another variation, a plurality of light tubes may be coupled to a single photodetector. When multiple photodetectors are employed, each may be coupled to one or a plurality of light tubes. Furthermore, the light tubes may be grouped together or spaced upon the photodetector(s) in any suitable configuration that allows receipt of light at a viewing angle that correlates with a high or maximum PI value. When more than one photodetector is included in the PPG sensor array, each photodetector can be coupled to a light tube(s) having the same or different preset viewing angles.

In some variations, information/data obtained by the PPG sensor array or wearable device may be transmitted to a remote location, e.g., a computer, doctor's office, etc. Here an antenna and wireless circuitry may also be included in the wearable devices. The wireless circuitry may include radio-frequency transceiver circuitry including, but not limited to, cellular telephone transceiver circuitry and wireless local area network transceiver circuitry.

The wearable devices disclosed herein may be generally used to measure PPG signals from a user. The PPG signals may then be used to extrapolate and monitor various types of physiological information/data. In some variations, the PPG signal is used to obtain information related to the heart rate of a user.

The acquisition of a PPG signal related to, e.g., heart rate, may be indicated to the user on the display of the wearable device. Heart rate may be indicated in any suitable manner by the wearable device. For example, heart rate may be indicated as a numerical value, a picture, or text on the device display, or be audibly provided by the wearable device. Heart rate may be indicated by combinations of any of the foregoing. In some variations, the wearable device may include a signal-strength indicator that is represented by the pulsing of an LED viewable by the user. Some implementations of the wearable device may use a light such as an LED to display the heart rate of the user by modulating the amplitude of the light emitted at the frequency of the user's heart rate. Other types of physiological data may be indicated in the same manner. Notifications relating to the obtained heart rate or other physiological data can also indicated in the same manner.

A processor may be included in the wearable device and be configured to execute algorithms for carrying out the various methods described herein and control the reception and manipulation of input and output data between components of wearable device, e.g., the light emitters and photodetectors. The processor can be a single-chip processor or can be implemented with multiple components.

The wearable devices may also include a power system for powering the various components. The power system may include a power management system, one or more power sources (e.g., battery, alternating current (AC)), a recharging system, a power failure detection circuit, a power converter or inverter, a power status indicator (e.g., a light-emitting diode (LED)) and any other components associated with the generation, management, and distribution of power in portable devices.

Methods for measuring a PPG signal and monitoring a physiological parameter of an individual are further disclosed herein. In some variations, the methods generally include securing a wearable device to a body region of the individual, the wearable device comprising a PPG sensor array, the PPG sensor array comprising an illumination system and a detection system; projecting light from the illumination system to a tissue layer within the body region; detecting light reflected from the tissue layer at a preset viewing angle associated with a high level of perfusion (and thus, a high level of pulsatile signal) using the detection system; and analyzing the PPG signal to determine a physiological parameter, where the preset viewing angle is determined by a viewing component. In one variation, the physiological parameter is heart rate. In another variation, the physiological parameter is oxygen saturation ($SpO_2$).

The wearable device may be secured to a body region by attachment mechanisms as previously disclosed herein, e.g., bands that may be attached to the user through the use of hooks and loops (e.g., Velcro), a clasp, and/or a band having memory of its shape, e.g., through the use of a spring metal band. When the wearable device is a wristwatch, the band may be made from a flexible material or have a structure that allows it to have an adjustable circumference. Body region of an individual where the device may be worn include a user's skin, wrist, arm, leg, etc. Accordingly, the wearable device may be a phone, wristwatch, arm or wristband, headband, or any wearable device suitable for collecting PPG signals or biometric information.

The preset viewing angle may depend on the spacing of the light emitter(s) and photodetector(s) of the PPG sensor array, and are generally associated with light received from tissue having a higher level of blood perfusion, and thus a higher level of pulsatile signal, as previously stated. One or more viewing components coupled to the PPG sensor array (e.g., the photodetector(s)), may be used to control the angle of reflected light viewed by the PPG sensor array to the certain viewing angles associated with a high level of pulsatile signal. The preset viewing angles may be equal to $\Theta_{PImax}$. Here the PPG signal received by the photodetector may subsequently be used to provide data related to the heart rate of the user. The preset viewing angles of the channeling components can be created by angled slats, angled light tubes, and similar structures.

As previously stated, a processor included in the wearable device will generally be configured to execute algorithms for deriving a physiological parameter from the PPG signal obtained using the viewing component. The algorithms may include steps that control the reception and manipulation of input and output data between components of the wearable device, e.g., the light emitters and photodetectors. For example, the algorithm may activate emission of light from select emitters of the illumination system as well as the control detection by select photodetectors of the detection system to create, e.g., various light emitter-detector pairs.

In some variations, the processor together with an operating system can operate to execute computer code and produce and use data. The computer code and data can reside within a program storage block that can be operatively coupled to the processor. The program storage block can generally provide a place to hold data that is being used by the operating system. The program storage block can be any non-transitory computer-readable storage medium, and can store, for example, history and/or pattern data relating to the PPG signal values measured by one or more photodetectors.

The foregoing description, for purpose of explanation, has been described with reference to specific embodiments. However, the illustrative discussions above are not intended to be exhaustive or to limit the invention to the precise forms disclosed. Many modifications and variations are possible in view of the above teachings. The embodiments were chosen and described in order to best explain the principles of the techniques and their practical applications. Others skilled in the art are thereby enabled to best utilize the techniques and various embodiments with various modifications as are suited to the particular use contemplated.

Although the disclosure and examples have been fully described with reference to the accompanying drawings, it is to be noted that various changes and modifications will become apparent to those skilled in the art. Such changes and modifications are to be understood as being included within the scope of the disclosure and examples as defined by the claims.

The present disclosure recognizes that personal information data, including biometric data, in the present technology, can be used to the benefit of users. For example, the use of biometric authentication data can be used for convenient access to device features without the use of passwords. In other examples, user biometric data is collected for providing users with feedback about their health or fitness levels. Further, other uses for personal information data, including biometric data that benefit the user are also contemplated by the present disclosure.

The present disclosure further contemplates that the entities responsible for the collection, analysis, disclosure, transfer, storage, or other use of such personal information data will comply with well-established privacy policies and/or privacy practices. In particular, such entities should implement and consistently use privacy policies and practices that are generally recognized as meeting or exceeding industry or governmental requirements for maintaining personal information data private and secure, including the use of data encryption and security methods that meets or exceeds industry or government standards. For example, personal information from users should be collected for legitimate and reasonable uses of the entity and not shared or sold outside of those legitimate uses. Further, such collection should occur only after receiving the informed consent of the users. Additionally, such entities would take any needed steps for safeguarding and securing access to such personal information data and ensuring that others with access to the personal information data adhere to their privacy policies and procedures. Further, such entities can subject themselves to evaluation by third parties to certify their adherence to widely accepted privacy policies and practices.

A wearable device for monitoring a physiological parameter of an individual is disclosed. The wearable device can comprise: a housing having a skin-contacting surface; one or more light emitters located to emit light from the skin-contacting surface; one or more light sensors, wherein each light sensor is configured to detect light that has interacted with a tissue region of the individual at one or more preselected angles of incidence; one or more viewing components optically coupled to the one or more light sensors and configured to allow light with the one or more preselected angles to pass through to the one or more light sensors; and a processor within the housing and in communication with the one or more light sensors, wherein the processor is configured to compute the physiological parameter based on light detected from the one or more light sensors. Additionally or alternatively, in some examples, each of the one or more viewing components allow light at a different preselected angle of incidence to pass through. Additionally or alternatively, in some examples, a first one or more viewing components is disposed over a first of the one or more light sensors and transmits light at a first preselected angle of incidence, and a second of the one or more viewing components is disposed over a second set of the one or more light sensors and transmits light at a second preselected angle of incidence. Additionally or alternatively, in some examples, a first of the one or more light sensors is configured to detect light having a first preselected angle of incidence, wherein the first preselected angle of incidence is selected based on a first separation distance between the first of the one or more light sensors and a first of the one or more light emitters configured to emit light of a first wavelength. Additionally or alternatively, in some examples, a second of the one or more light sensors is configured to detect light having a second preselected angle of incidence, wherein the second preselected angle of incidence is selected based on a second separation distance between the second of the one or more light sensors and a second of the one or more light emitters configured to emit light of a second wavelength. Additionally or alternatively, in some examples, the first preselected angle of incidence is different from the second preselected angle of incidence. Additionally or alternatively, in some examples, the first wavelength is the same as the second wavelength, the first separation distance is different from the second separation distance, and the first preselected angle of incidence is different from the second preselected angle of incidence. Additionally or alternatively, in some examples, the first wavelength is different from the second wavelength, the first separation distance is the same as the second separation distance, and the first preselected angle of incidence is different from the second preselected angle of incidence. Additionally or alternatively, in some examples, the first wavelength is different from the second wavelength, the first separation distance is different from the second separation distance, and the first preselected angle of incidence is different from the second preselected angle of incidence. Additionally or alternatively, in some examples, the first wavelength is different from the second wavelength, the first distance is different from the second distance, and the first preselected angle of incidence is the same as the second preselected angle of incidence. Additionally or alternatively, in some examples, the processor receives first data from the first of the one or more light sensors and second data from the second of the one or more light sensors, wherein the first data and the second data each comprise physiological data pertaining to the same tissue region, and wherein the processor is configured to compute the physiological parameter based on the physiological data. Additionally or alternatively, in some examples, the one or more light sensors include a first set of light sensors configured to measure a first wavelength and a second set of light sensors configured to measure a second wavelength, wherein at least one of the first set of light sensors is configured to have the same preselected angle as at least one of the second set of light sensors, and further wherein at least one of the first set of light sensors is configured to have a different preselected angle than another of the first set of light sensors. Additionally or alternatively, in some examples, the first set of light sensors is interleaved with the second set of light sensors. Additionally or alternatively, in some examples, the one or more light sensors includes a first set of light sensors configured to measure a first tissue region and a second set of light sensors configured to measure a second tissue region, wherein at least one of the first set of light sensors is coupled to a first of the one or more viewing component, the first of the one or more viewing components having the same preselected angle of incidence as a second of the one or more viewing components, the second of the one or more viewing components coupled to at least one of the second set of light sensors. Additionally or alternatively, in some examples, the first of the one or more viewing components is optically coupled to a first of the one or more light emitters and the second of the one or more viewing components is optically coupled to a second of the one or more light emitters, a separation distance between the first of the one or more viewing components and the first of the one or more light emitters being the same as a separation distance from the second of the one or more viewing components and the second of the one or more light emitters. Additionally or alternatively, in some examples, the one or more light sensors are configured as an array of light sensors, each light sensor optically coupled to a different of the one or more viewing components, each of the one or more viewing components having a different preselected angle.

A method of measuring a physiological parameter of an individual is disclosed. The method can comprise: selectively allowing light having one or more preselected angles of incidence to pass through one or more viewing components; detecting the light that has interacted with a tissue region of the individual using one or more light sensors; and computing the physiological parameter based on the light detected from the one or more light sensors. Additionally or alternatively, in some examples, the method further comprises: emitting a first light using a first of the one or more light emitters, a portion of the first light included in the light; emitting a second light using a second of the one or more light emitters, a portion of the second light included in the light; optically coupling a first of the one or more light sensors to a first of the one or more viewing components; optically coupling a second of the one or more light sensors to a second of the one or more viewing components; locating the first of the one or more light emitters a separation distance from the first of the one or more viewing components; and locating the second of the one or more light emitters the separation distance from the second of the one or more viewing components. Additionally or alternatively, in some examples, computing the physiological parameter includes selecting between a signal associated with the first light and a signal associated with the second light. Additionally or alternatively, in some examples, the method further comprises: associating each of the one or more viewing components to one of the one or more preselected angles of incidence; associating each of the one or more light sensors to one of the one or more viewing components; and associating each signal from the one or more light sensors to a different layer in a skin of the individual.

Despite the foregoing, the present disclosure also contemplates embodiments in which users selectively block the use of, or access to, personal information data, including biometric data. That is, the present disclosure contemplates that hardware and/or software elements can be provided to prevent or block access to such personal information data. For example, in the case of biometric authentication methods, the present technology can be configured to allow users to optionally bypass biometric authentication steps by providing secure information such as passwords, personal identification numbers (PINS), touch gestures, or other authentication methods, alone or in combination, known to those of skill in the art. In another example, users can select to remove, disable, or restrict access to certain health-related applications collecting users' personal health or fitness data.

What is claimed is:

1. A wearable device for monitoring a physiological parameter of a user, comprising:
   a housing;
   a light emitter positioned within the housing and configured to emit light towards a skin of the user when the housing is worn by the user;
   a first light detector positioned within the housing at a first location with respect to the light emitter;
   a second light detector positioned within the housing at a second location with respect to the light emitter;
   a viewing component coupled to the first light detector and configured to:
      allow a first portion of the emitted light that intersects the viewing component at a preset viewing angle to pass to the first light detector; and
      block a second portion of the emitted light that intersects the viewing component at angles other than the preset viewing angle, wherein the preset viewing angle is based at least in part on a separation distance between the light emitter and the first light detector; and
   a processor positioned within the housing and configured to:
      receive a first signal from the first light detector based on the first light detector receiving the first portion of the light;
      receive a second signal from the second light detector based on the second light detector receiving a third portion of the light;
      compare a first strength of the first signal to a second strength of the second signal; and
      compute the physiological parameter of the user using the first signal or the second signal with the greater of the first strength or the second strength.

2. The wearable device of claim 1, wherein:
   the first light detector defines a light receiving surface;
   the viewing component comprises multiple slats; and
   the multiple slats are oriented at the preset viewing angle with respect to the light receiving surface.

3. The wearable device of claim 2, wherein the multiple slats are positioned over an entirety of the light receiving surface.

4. The wearable device of claim 1, wherein the preset viewing angle defined by the viewing component:
   prevents light from a first tissue layer from reaching the first light detector; and allows light from a second tissue layer, deeper than the first tissue layer, to reach the first light detector.

5. The wearable device of claim 1, further comprising a band coupled with the housing, wherein:
the first light detector comprises a light receiving surface; and
the band is operative to wrap around a portion of the user to position the light receiving surface against the skin of the user.

6. The wearable device of claim 1, wherein:
the first light detector is configured to receive light from a first tissue depth; and
the second light detector is configured to receive light from a second tissue depth that is greater than the first tissue depth.

7. A wearable device for detecting a physiological parameter of a user, comprising:
a housing;
a light emitter coupled with the housing and configured to emit light towards a skin of the user when the wearable device is contacting the user;
a first light detector coupled with the housing and operative to detect a first portion of the emitted light that has interacted with the skin of the user;
a second light detector coupled to the housing and operative to detect a second portion of the emitted light that has interacted with the skin of the user;
a viewing component coupled to a light receiving surface of the first light detector and configured to prevent a portion of the light that is outside a preset viewing angle from reaching the light detector; and
a processor positioned within the housing and configured to:
receive a first signal from the first light detector based on the detected first portion of the emitted light;
receive a second signal from the second light detector based on the detected second portion of the emitted light;
compare a first strength of the first signal to a second strength of the second signal; and
determine the physiological parameter of the user using the first signal or the second signal with the greater of the first strength or the second strength.

8. The wearable device of claim 7, further comprising a touch screen, wherein the touch screen is operative to display a visual output indicative of the physiological parameter of the user.

9. The wearable device of claim 8, wherein:
the touch screen is operative to receive a touch input from the user; and
in response to receiving the touch input, the wearable device is configured to determine the physiological parameter of the user.

10. The wearable device of claim 7, wherein the physiological parameter is a heart rate of the user.

11. The wearable device of claim 7, further comprising a band coupled to the housing, wherein:
the band is configured to position a first portion of the housing against the skin of the user;
the light emitter is positioned on the first portion of the housing; and
the first and second light detectors are positioned on the first portion of the housing.

12. The wearable device of claim 7, wherein:
the viewing component comprises multiple slats coupled with the light receiving surface of the first light detector; and
the multiple slats are oriented at an angle with respect to the light receiving surface.

13. The wearable device of claim 12, wherein the angle of the multiple slats corresponds to the preset viewing angle.

14. A wearable device for monitoring a physiological parameter of a user, comprising:
a housing;
a light emitter coupled to the housing and operative to emit light toward a skin of the user when the wearable device is worn by the user;
an array of light detectors including at least two detectors that are operative to detect a portion of the light that has interacted with the skin of the user, wherein each light detector in the array of light detectors comprises a viewing component coupled to the light detector and configured to:
allow a first portion of the light that intersects the respective viewing component at a preset viewing angle to pass to the light detector; and
block a second portion of the light that intersects the respective viewing component at angles other than the preset viewing angle; and
a processor positioned within the housing and configured to:
receive a signal from each light detector in the array of light detectors based on the first portion of the light detected by each respective light detector in the array of light detectors;
determine a strength of each of the received signals; and
compute the physiological parameter of the user using the signal with the greater strength.

15. The wearable device of claim 14, wherein the preset viewing angle of the viewing component for each light detector in the array of light detectors is based on a position of the respective light detector relative to the light emitter.

16. The wearable device of claim 15, wherein the preset viewing angle of the viewing component for each light detector is different.

17. The wearable device of claim 15, wherein the preset viewing angle of the viewing component for each light detector is configured such that the first portion of the light received by each light detector is from substantially a same tissue depth.

* * * * *